US00PP08324P

United States Patent [19]

Vletter

[11] Patent Number: Plant 8,324

[45] Date of Patent: Jul. 27, 1993

[54] LILY PLANT NAMED CARTOUCHE

[75] Inventor: Floris Vletter, Rijnsburg, Netherlands

[73] Assignee: Gebr. Vletter & J. A., Rijnsburg, Netherlands

[21] Appl. No.: 795,955

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct lily plant named Cartouche, characterized by its generally pink base color with white edges and tips and bright red-purple midvein; orange-brown pollen, large flowers, and floriferous habit.

1 Drawing Sheet

The present invention comprises a new and distinct cultivar of lily, botanically known as Lilium, known commercially as Lilium oriental hybrid, and hereinafter referred to by the cultivar name Cartouche. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the general objective of creating new lily cultivars having attractive flower color and having all the other desired attributes for cut-flower production.

The new cultivar was originated from a hybridization made by the inventor in a controlled breeding program in Rijnsburg, The Netherlands in 1981. The female parent was the cultivar Stargazer. The male parent was an unnamed seedling.

The new cultivar was discovered and selected as one flowering plant within the progeny of the stated cross by the inventor in July 1981 in a controlled environment in Rijnsburg, The Netherlands.

The first act of asexual reproduction of the new cultivar was accomplished by the inventor when scales were taken from the initial selection in 1985 in a controlled environment in Rijnsburg, The Netherlands.

Horticultural examination of selected units has demonstrated that the combination of characteristics as herein disclosed for the new cultivar are firmly fixed and are retained through successive generations of asexual reproduction.

The new cultivar has not been observed under all possible environmental conditions. The phenotype may vary somewhat with variations in environment such as temperature, light intensity, and day length, without, however, varying in the genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Generally pink main flower color, accented by white edges and tips, and a bright red stripe or streak along the midvein and to varying degrees on either side of the midvein.
2. Contrasting orange-brown pollen.

3. Numerous red markings spots on each tepal.
4. Large flowers.
5. Floriferous habit.

Of the many commercial cultivars known to the present inventor, the most similar in comparison to the new cultivar is Berlin, disclosed in a pending plant patent application of the present inventor. When flowering is forced under natural light, Cartouche produces an inflorescence approximately 12 days earlier than Stargazer, grown under the same conditions. Cartouche is fertile. In comparison to Berlin, Cartouche has stronger and shorter stems; its flowers are more pronounced in that there is strong longitudinal undulation along the edges of the flowers and strong tip reflexing, and there is more color diversity due to the white edges and tip, the generally pink main color, and the bright streaking.

The accompanying color photographic drawing shows typical flower characteristics of the new cultivar, with colors being as true as possible with illustrations of this type. The photo is a front perspective view showing two open flowers and several buds at various stages.

In the following description, color references are made to The Royal Horticultural Society (RHS) Colour Chart. The color values were determined at Wageningen in 1989–1990 and at Rijnsburg in July 1991.

Origin: Seedling from Breeding Program.

Parentage:

*Seed parent.*—Stargazer.

*Pollen parent.*—Unnamed seedling.

Classification:

*Botanical.*—Lilium.

*Commercial.*—Oriental hybrid.

The plant:

*Form.*—A single stem carrying numerous pedicels alternately arranged.

*Height.*—Height is medium to tall, being approximately 125 cm on opening of anthers of first flower.

*Growth habit.*—Vigorous.

*Stem.*—Circular in transverse section; internodal length uniform (1–1.5 cm); color light green 145B with lighter spots.

*Foliage.*—Quantity: Normal, with number depending on growing conditions. Size of leaf: Mature leaves are short to medium in length (13 cm) and medium in width (3 cm). Shape of leaves: Ovate. Texture: Smooth with weak glossiness on upper side. Color: 137A.

*Bulbs.*—Size: Outlet 6–30 cm. Color: Purple, white and yellow.

*Roots.*—Both stem and contractile present.

The bud:

*Form.*—Tapering (like a lancet).

*Size.*—11 cm in length.

*Opening.*—Unfolds normally.

*Color.*—Light pink prior to opening.

*Tepals.*—Folded, three visible.

The flower:

*Blooming habit.*—Raceme.

*Size.*—Approximately 19 cm in diameter depending on growing conditions.

*Borne.*—Upright to horizontal.

*Shape.*—Generally in form of hexagonal star when viewed from top.

*Tepalage.*—Number of tepals: Six. Arrangement: Three inner and three outer each with marginal undulation. Color: Upper surface: Pink 62B with bright red streaking along midvein and white edges and tips. Lower surface: Pink 65B; base almost white 155B. Spotting or marking: Present, dark purple; yellow to green colored strip at base of each tepal.

*Nectaries and papillae.*—Present.

*Pedicel.*—Length: 7 cm (of first flower). Color: Medium green with anthocyanin. Form: Slightly curved.

*Texture.*—Papillose.

*Disease resistance.*—No disease problems noted to date.

*Fragrance.*—Present; medium.

*Lasting quality.*—Excellent.

Reproductive organs:

*Stamens, anthers.*—Arrangement: Anthers form a generally circular pattern. Length: Short to medium (8.5 cm). Number: Six. Filaments: Green.

*Pollen color.*—Orange brown.

*Anther color.*—Reddish brown.

*Pistils.*—One with green style; total length of pistil is 10.5 cm.

*Stigma.*—Color purple to light purple.

*Ovaries.*—Triangular in shape; other characteristics typical of oriental lily varieties.

I claim:

1. A new and distinct cultivar of lily plant named Cartouche, as illustrated and described.

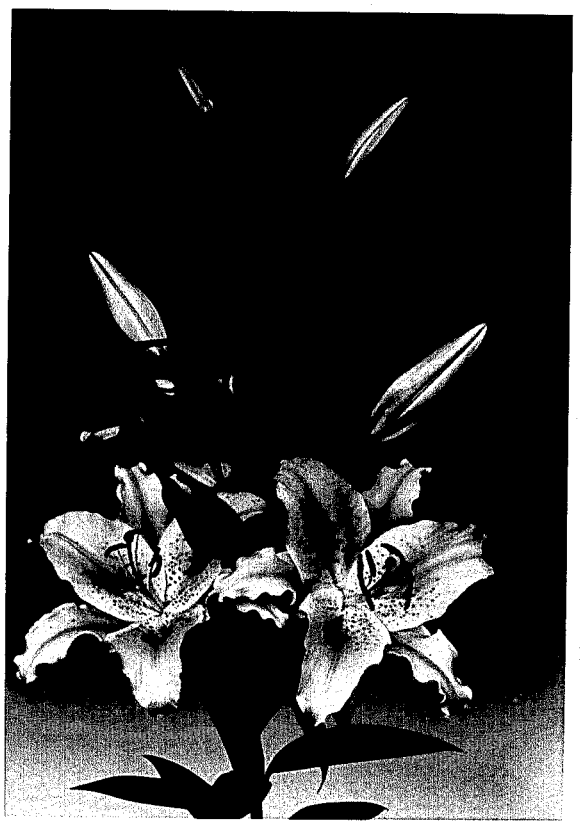

* * * * *